US009567271B2

(12) United States Patent
Kumar et al.

(10) Patent No.: US 9,567,271 B2
(45) Date of Patent: Feb. 14, 2017

(54) PROCESS FOR THE RECOVERY OF PARAFFINS FROM AN ISOMERIZATION EFFLUENT

(71) Applicant: UOP LLC, Des Plaines, IL (US)

(72) Inventors: Manoj Kumar, Haryana (IN); David James Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 198 days.

(21) Appl. No.: 14/476,256

(22) Filed: Sep. 3, 2014

(65) Prior Publication Data

US 2016/0060191 A1 Mar. 3, 2016

(51) Int. Cl.
| | |
|---|---|
| C07C 5/27 | (2006.01) |
| C07C 7/00 | (2006.01) |
| C10G 45/58 | (2006.01) |
| C10G 65/04 | (2006.01) |
| C10G 7/02 | (2006.01) |

(52) U.S. Cl.
CPC ............. C07C 5/277 (2013.01); C07C 7/00 (2013.01); C10G 7/02 (2013.01); C10G 45/58 (2013.01); C10G 65/043 (2013.01)

(58) Field of Classification Search
USPC ............ 585/748, 751, 700 S, 800 S
See application file for complete search history.

(56) References Cited

U.S. PATENT DOCUMENTS

| | | | |
|---|---|---|---|
| 4,673,488 A | 6/1987 | Turner et al. | |
| 5,082,989 A | 1/1992 | Johnson | |
| 5,227,554 A * | 7/1993 | Chou | C07C 5/226 585/738 |
| 2011/0275877 A1* | 11/2011 | Kaul | C07C 5/2767 585/820 |
| 2014/0128649 A1 | 5/2014 | Kumar et al. | |

FOREIGN PATENT DOCUMENTS

| | | |
|---|---|---|
| RU | 2368594 C2 | 9/2009 |
| WO | 2012021341 A2 | 2/2012 |
| WO | 2012097051 A1 | 7/2012 |
| WO | 2014074266 A1 | 5/2014 |

OTHER PUBLICATIONS

Search Report dated Dec. 3, 2015 for corresponding PCT Appl. No. PCT/US2015/037911.

* cited by examiner

Primary Examiner — Sharon Pregler

(57) ABSTRACT

A process for the recovery of $C_4$ hydrocarbons from a $C_5/C_6$ isomerization zone. A portion of the effluent stream from the $C_5/C_6$ isomerization zone comprising $C_4$ hydrocarbons is combined in a stabilizer section with an effluent from a $C_4$ isomerization zone. In order to increase the $C_4$ hydrocarbons in the effluent stream from the $C_5/C_6$ isomerization zone, a chilling zone may be used.

20 Claims, 2 Drawing Sheets

PROCESS FOR THE RECOVERY OF PARAFFINS FROM AN ISOMERIZATION EFFLUENT

FIELD OF THE INVENTION

Figure 1:
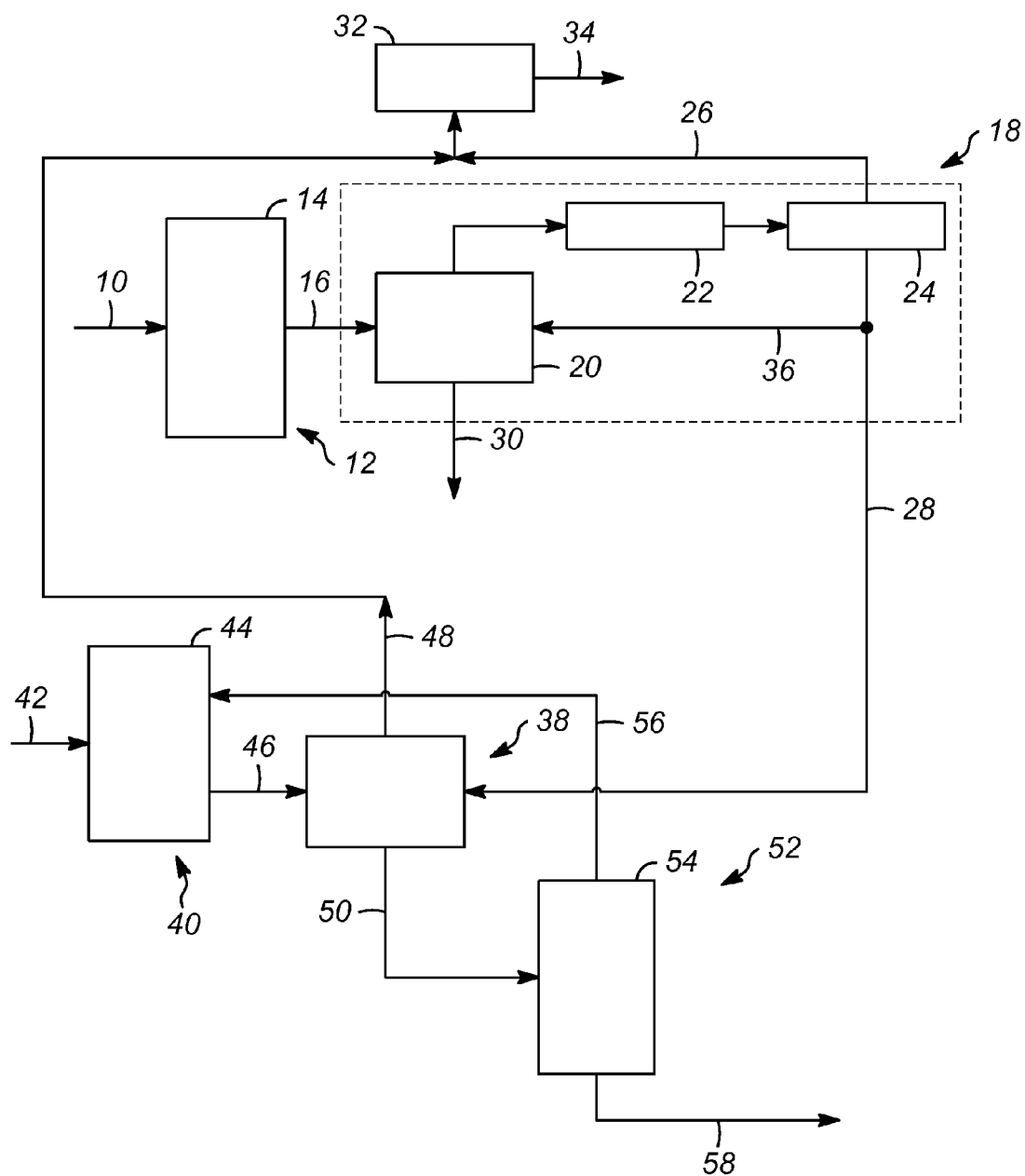

This invention relates generally to a process for the recovery of paraffins from an isomerization effluent, and more particularly to the recovery of $C_4$ hydrocarbons.

BACKGROUND OF THE INVENTION

Petroleum refining and petrochemical processes frequently involve isomerization processes. Isomerization processes are widely used by many refiners and processers to rearrange the molecular structure of hydrocarbons. In some instances it is more desirable to have more highly branched hydrocarbons. Generally, these more highly branched hydrocarbons have relatively high octane ratings. In other instances it is more desirable to have straight chain paraffins, for example for feed to a stream cracker or for production of chemicals. Accordingly, isomerization can involve conversion of iso-paraffins into normal paraffins or the conversion of normal paraffins into iso-paraffins. Additionally, due to equilibrium factors, various hydrocarbon feed streams are isomerized in different zones.

For example, $C_5$ and $C_6$ hydrocarbons streams are often isomerized in the same zone. When the isomerization comprises of converting iso-paraffins into normal paraffins, a large amount of $C_4$ hydrocarbons may be formed as a product of cracking and disproportionation reactions.

The isomerization zone typically includes a stabilizer to separate the effluent from the isomerization zone. As a result of the high amount of light ends in the effluent, the stabilizer requires an LPG draw ($C_3$/$C_4$ hydrocarbons). However, since the LPG draw contains some amount of chloride, typically as HCl, the LPG draw cannot be directly routed to, for example, a saturated gas plant, as the LPG draw contains some amount of chlorides. Therefore, a stripping zone is used to remove the light ends ($C_2$− hydrocarbons) and chlorides. Then, the LPG draw can be passed, along with light ends from other sources, to the saturated gas plant where the combined stream can be cleaned (sulfur removed) and fractionated. Any $C_4$ hydrocarbons could be recovered and recycled back to be isomerized in a $C_4$ hydrocarbons isomerization unit.

It is believed that a more effective and efficient process for recovering the $C_4$ hydrocarbons would be desirable.

SUMMARY OF THE INVENTION

A first embodiment of the invention may be characterized as a process for the recovery of $C_4$ hydrocarbons comprising: stabilizing and separating a first effluent stream in a first stabilization zone into an overhead stream, a $C_4$− liquid stream, and a bottoms stream, wherein the first effluent stream is from a first isomerization zone; stabilizing a second effluent stream from a second isomerization zone in a second stabilization zone; passing at least a portion of the $C_4$− liquid stream to the second stabilization zone; and, separating the second effluent stream and the at least a portion of the $C_4$− liquid stream into a $C_4$ stream and a $C_3$− stream.

In at least one embodiment, the process further includes separating the $C_4$ stream into an i$C_4$ stream and a n$C_4$ stream. It is contemplated that the process also includes passing the i$C_4$ stream to the second isomerization zone.

In some embodiments, the first stabilization zone comprises a stabilizer, a receiving zone and a chilling zone.

In at least one embodiment, the process further includes passing a $C_4$− stream from the stabilizer to the receiver, separating the $C_4$− stream in the receiver into a vapor stream and a liquid stream. The liquid stream comprises the $C_4$− liquid stream and the vapor stream comprises mostly $C_3$− hydrocarbons. It is contemplated that the process also include cooling the vapor stream from the receiver in the chilling zone. It is further contemplated that the process includes combining a portion of the vapor stream from the receiver and the $C_3$− stream of the second stabilization zone.

In some embodiments, the process includes operating the first isomerization zone under isomerization conditions, in the presence of a catalyst, to convert iso-paraffins into normal paraffins. It is contemplated that the iso-paraffins comprise iso-pentane and iso-hexane. It is further contemplated that the process also includes operating the second isomerization zone under isomerization conditions, in the presence of a catalyst, to convert iso-butane into normal butane.

A second aspect of the present invention may be characterized as a process for the recovery of $C_4$ hydrocarbons comprising: passing a $C_4$− liquid stream to a stabilization zone, the liquid $C_4$− stream comprising at least a portion of an effluent from a first isomerization zone operated under isomerization conditions to convert iso-paraffins into normal paraffins; passing at least a portion of a second effluent stream from a second isomerization zone to the stabilization zone, the second effluent stream comprising $C_4$− hydrocarbons, wherein the second isomerization zone is operated under isomerization conditions to convert iso-butane into normal butane; and, separating the at least a portion of the second effluent stream and the $C_4$− liquid stream into a $C_4$ stream and a $C_3$− stream.

In at least one embodiment, the iso-paraffins comprise iso-pentane and iso-hexane. It is also contemplated that the process includes cooling a portion of the effluent from the first isomerization zone to increase an amount of $C_4$ hydrocarbons in the liquid $C_4$− stream.

In some embodiments, the process further includes combining a first vapor stream from the stabilization zone comprising a $C_3$− stream with a second vapor stream comprising a second $C_3$− stream. It is contemplated that the second $C_3$− stream comprises a portion of the effluent from the first isomerization zone.

It still other embodiments the process further includes separating the $C_4$ stream from the stabilization zone into an i$C_4$ stream and an n$C_4$ stream. It is further contemplated that the process also includes passing the i$C_4$ stream to the second isomerization zone.

In at least one embodiment, the process also includes separating the effluent from the first isomerization zone into a $C_4$− stream and a $C_5$+ stream and separating the $C_4$− liquid stream from at least a portion of the $C_4$− stream. It is further contemplated that the process includes separating the $C_4$− stream into the $C_4$− liquid stream and a $C_3$− vapor stream. It is contemplated that the process also includes increasing an amount of $C_4$ in the $C_4$− liquid stream by cooling the $C_4$− stream.

Additional objects, embodiments, and details of the invention are set forth in the following detailed description of the invention.

DETAILED DESCRIPTION OF THE DRAWINGS

Figure 2:
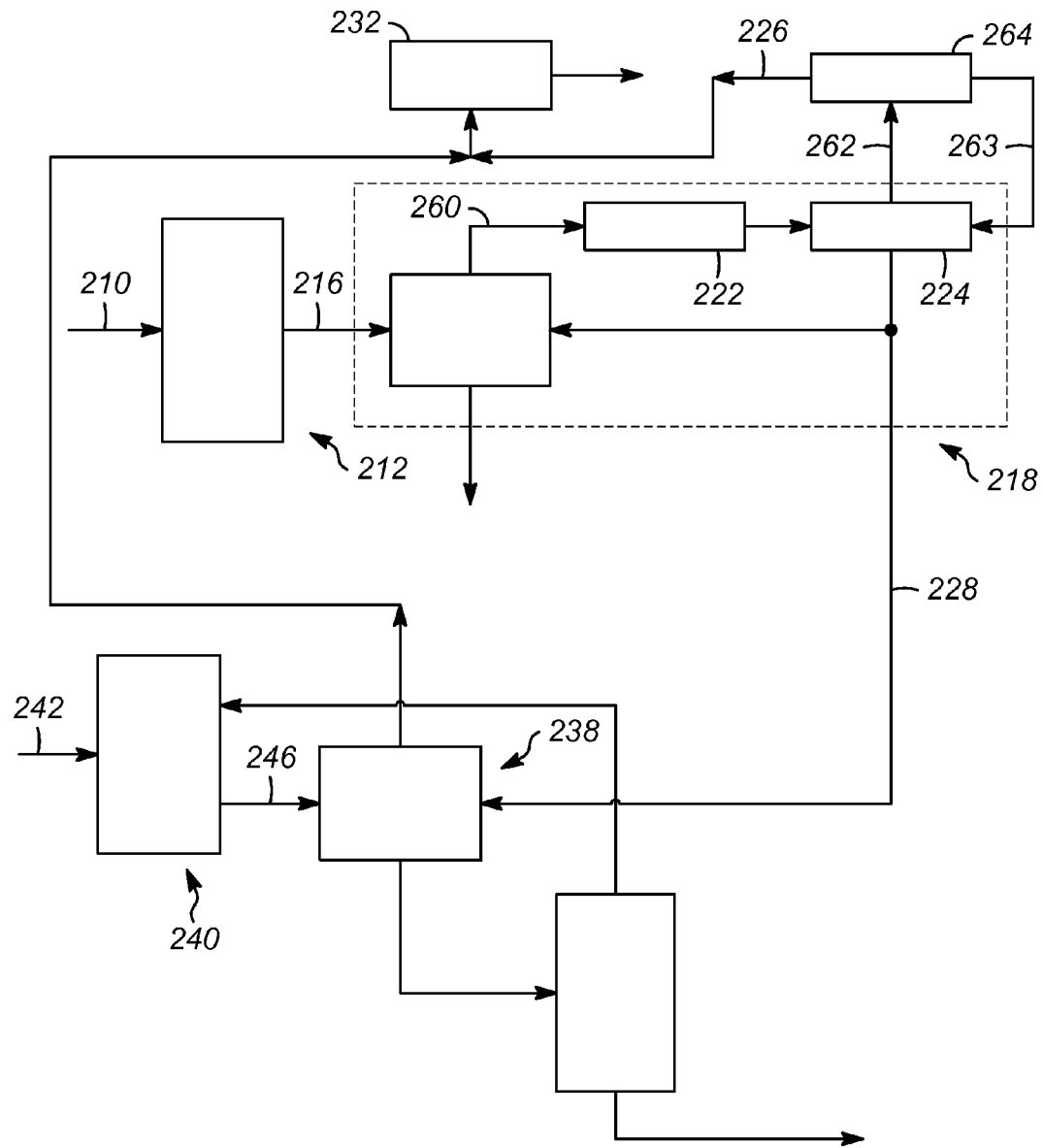

The drawings are simplified process diagrams in which:

FIG. 1 shows a process according to one or more embodiments of the present invention; and, FIG. 2 shows another process according to one or more embodiments of the present invention.

DETAILED DESCRIPTION OF THE INVENTION

One or more methods have been developed which increase the recovery of $C_4$ hydrocarbons from the isomerization of iso-pentane and iso-hexane to normal paraffins. In some of the processes of the present invention, no additional equipment is required. In fact, in many instances, the processes reduce the amount and size of the equipment that is typically used. Thus, such processes not only increase the product recovery, but also lower the capital expenditures and operating expenses associated with same.

With reference to the attached drawings, one or more exemplary processes will now be described with the understanding that following detailed description is merely exemplary in nature and is not intended to limit the various embodiments or the application and uses thereof. Furthermore, there is no intention to be bound by any theory presented in the preceding background or the following detailed description.

As shown in FIG. 1, one or more processes according to the present invention comprise a first feed stream 10 being passed to a first isomerization zone 12. In a preferred embodiment the first feed steam 10 comprises a $C_5+$ hydrocarbon stream (meaning hydrocarbons with 5 or more carbon atoms). The $C_5+$ hydrocarbon stream may comprise iso- or branched paraffinic $C_5/C_6$ hydrocarbons and may further include normal or unbranched paraffinic $C_5/C_6$ hydrocarbons, such as normal pentane and normal hexane.

Although not illustrated, hydrogen-containing gas and a chloride promoter are typically introduced to the feed stream 10. The feed stream 10, and hydrogen-containing gas, may be passed (together or separately) through a dryer(s), a heat exchanger(s), and/or a heater(s) so that the stream(s) are dry and heated when passed into the isomerization zone 12. The chloride promoter may be added after the feed stream 10 has passed through the dryer(s)

In a preferred embodiment, the isomerization zone 12 comprises at least one fixed-bed catalytic reactor 14 operating at conditions to isomerize iso-paraffins into normal paraffins. Typical operating conditions include a temperature of from about 90° C. to about 210° C. and pressure of 3100 kPa(g). The isomerization catalyst is typically activated by HCl by the decomposition of chloride promoter to form a high-activity chloride-promoted isomerization catalyst. Non-limiting examples of the isomerization catalyst include alumina catalyst, platinum aluminum catalyst, and the like that can be chlorinated. In a most preferred embodiment, a chloride-promoted isomerization catalyst in the presence of hydrogen is effective to isomerize the branched pentane and hexane into normal paraffins (e.g., normal pentane and normal hexane) to produce an isomerization zone effluent 16.

The isomerization zone effluent 16 contains normal and some branched $C_5/C_6$ hydrocarbons, $C_4$ hydrocarbons, $C_3$ hydrocarbons, some naphthenes and $C_7$ paraffinic hydrocarbons, hydrogen (e.g., unreacted hydrogen), HCl, and possibly other chloride-containing compounds. Some of these compounds may have been present in the feed stream 10, while others may have been generated in the isomerization zone 12 due to various reactions, like disproportionation reactions and cracking of larger compounds.

Accordingly, the isomerization zone effluent 16 is passed to a stabilization zone 18. As shown, the stabilization zone 18 typically includes a stabilizer 20, a condenser 22 and a receiver 24. In an exemplary embodiment, the stabilization zone 18, more specifically, the receiver 24, is operating at a temperature of from about 35° C. to about 45° C. and a pressure of from about 1000 kPag to about 1700 kPag, preferably between about 1200 kPag to about 1500 kPag.

In the stabilization zone 18, the isomerization zone effluent 16 is separated into a vapor stream 26 (comprising mostly $C_3$-hydrocarbons), a $C_4$- hydrocarbon liquid stream 28, and a $C_5+$ hydrocarbon stream 30.

The $C_5+$ hydrocarbon stream 30 is typically rich in normal $C_5+$ hydrocarbons, such as normal pentanes and normal hexanes, and is removed from the process as product and may be passed to further downstream processing and separation zones for recovery.

In order to remove HCl, the vapor stream 26 is passed to a scrubbing zone 32. The scrubbing zone 32 scrubs the vapor stream 26 by neutralizing the HCl contained therein. As is known, the vapor stream 26 is typically scrubbed with caustic to form a neutralized gas stream 34. The neutralized gas stream 34 may be passed to downstream processing, for example to a saturated gas plant to recover $C_3$- hydrocarbons (depending on the saturated gas plant, there may be a butane, propane, $C_2$- hydrocarbons, and sometimes hydrogen stream).

The $C_4$- hydrocarbons liquid stream 28 typically includes $C_4$ hydrocarbons, as well as some $C_3$- hydrocarbons, hydrogen, and HCl. A portion 36 of the $C_4$- hydrocarbons liquid stream can be passed back as reflux to the stabilizer 18. Unlike conventional process which require a scrubber on the $C_4$- hydrocarbons liquid stream 28 (for example to recover the scrubbed stream as LPG), in the present invention, the $C_4$- -hydrocarbons liquid stream 28 is passed to a second stabilization zone 38 that is disposed downstream of a second isomerization zone 40.

The second isomerization zone 40 receives a second feed stream 42. In a preferred embodiment, the second feed stream 42 is a $C_4$ hydrocarbons stream which comprises normal and branched paraffinic $C_4$ hydrocarbons, such as normal butane and isobutane. Similar to the above, although not illustrated, a hydrogen-containing gas and a chloride promoter (e.g., containing perchloroethylene or the like) are typically introduced to the second feed stream 42. The second feed stream 42 may be passed (together or separately with the hydrogen-containing gas) through a dryer(s), a heat exchanger(s), and/or a heater(s) so that the stream is dry and heated while advancing through the second isomerization zone 40. After the dryer(s), the chloride promoter may be added to the feed stream 42.

In a preferred embodiment, the second isomerization zone 40 also comprises at least one fixed-bed catalytic reactor 44 operating at conditions to isomerize iso-paraffins into normal paraffins. Typical conditions in the second isomerization zone 40 include an operating temperature of from about 90° C. to about 210° C. and pressure of about 3,100 kPag. Additionally, the isomerization catalyst is preferably activated by HCl by the decomposition of chloride promoter to form a high-activity chloride-promoted isomerization catalyst as described above in relation to the first isomerization zone 12. The chloride-promoted isomerization catalyst in the presence of hydrogen is effective to isomerize the branched paraffins to normal paraffins (e.g., normal butane) to produce a second isomerization zone effluent 46.

The second isomerization zone effluent 46 contains branched and unbranched $C_4$ hydrocarbons, $C_3-$ hydrocarbons, hydrogen (e.g., unreacted hydrogen), HCl, and possibly other chloride-containing compounds and other hydrocarbons such as $C_5$ hydrocarbons and some trace $C_6+$ hydrocarbons. The second isomerization zone effluent 46 is passed to the second stabilization zone 38.

In the second stabilization zone 38, the second isomerization zone effluent 46 and the $C_4-$ hydrocarbons liquid stream 28 are separated into a $C_3-$ hydrocarbons stream 48 and a $C_4$ hydrocarbons stream 50. The $C_3-$ hydrocarbons stream 48 will also include HCl and can be passed to the scrubbing zone 32 and processed along with the vapor stream 26 from the first stabilization zone 18. The second stabilization zone 38 is operating at a temperature in the range of about 35° C. to about 45° C. and a pressure in the range of about 2,000 kPag to about 2,300 kPag.

The $C_4$ hydrocarbons stream 50 may be passed to a separation zone 52, preferably which includes a fractionation column 54, which can be used to separate iso-paraffins from normal paraffins. In embodiments in which the second feed stream 42 is a $C_4$ hydrocarbons stream, an overhead stream 56 from the separation zone 52 comprises iso-butane and a bottoms stream 58 from the separation zone 52 comprises normal butane, and may also include some $C_5+$ hydrocarbons produced, for example, in the second isomerization zone 40. The overhead stream 56 may be passed back to the second isomerization zone 40. The bottoms stream 58 may be recovered as the desired normal paraffin product and passed to further processing. This process has allowed for the recovery of the $C_4$ hydrocarbons produced in the first isomerization zone without requiring an additional processing unit to remove the HCl from the first isomerization zone effluent.

It is further contemplated that the $C_4$ hydrocarbon recovery can be increased even further by chilling or cooling a portion of the effluent from the first isomerization zone. Accordingly, a second exemplary process is shown in FIG. 2, in which similar elements from the embodiment of FIG. 1 have the same reference numeral with the exception of an additional "2".

As shown in FIG. 2, this embodiment of the invention also includes two feed streams 210, 242, each one being passed to an isomerization zone 212, 240. Each isomerization zone 212, 240 provides an effluent stream 216, 246 that is passed to a stabilization zone 218, 238. A portion 260 of the first isomerization zone effluent stream 216 is passed, preferably via a condenser 222, to a receiver 224. The portion 260 preferably comprises $C_4-$ hydrocarbons, as well as hydrogen and HCl.

In the receiver 224, the compounds in the portion 260 of first isomerization zone effluent stream 216 are separated into a $C_4$ hydrocarbons liquid stream 228, and a $C_4-$ hydrocarbons stream 262. In order to increase the amount of $C_4$ hydrocarbons in the $C_4$ hydrocarbons liquid stream 228, the $C_4-$ hydrocarbons stream 262 is passed to a chilling zone 264 where the $C_4-$ hydrocarbons stream 262 is cooled to a temperature between 4° C. and −40° C., and preferably to a temperature of approximately −17.7° C. (0° F.). From the chilling zone 264, a $C_3-$ -hydrocarbons vapor stream 226 is passed to a scrubbing zone 232 to remove HCl. A chilled stream 263 is passed back from the chilling zone 264 to the receiver 224. The compounds in the chilled stream 263, mostly $C_4$ hydrocarbons, may be separated into the $C_4$ hydrocarbons liquid stream 228 and the $C_4-$ hydrocarbons stream 262.

The remaining portions of the embodiment in FIG. 2 are the same as the embodiment shown in FIG. 1, and thus, that description is incorporated herein.

In a theoretical modeling based upon TABLE 1, below, a process according to the embodiment shown in FIG. 1 allowed for a recovery of approximately 5,500 kg/h (5.5 T/h) and a recovery of approximately 20% of the $C_4$ hydrocarbons from the first isomerization zone passed to the stabilization zone to be separated with the second isomerization zone effluent.

TABLE 1

| Component | Mass Flow at Feed into the First Stabilization Zone in kg/h (lbs/h) | Mass Flow in $C_{4-}$ liquid stream in kg/h (lbs/h) |
|---|---|---|
| $C_3$ | 7,277 (16,043) | 755 (1,666) |
| i-$C_4$ | 21,191 (46,719) | 4,221 (9305) |
| n-$C_4$ | 7,800 (17,197) | 1,901 (4191) |

In a second theoretical modeling based upon TABLE 2, a process according to the embodiment shown in FIG. 2 with a chilling zone, approximately 24,500 kg/h (24.5 T/h) $C_4$ hydrocarbons were recovered, representing 85% of the $C_4$ hydrocarbons from the first isomerization zone, is passed to the second stabilization zone to be separated with the second isomerization zone effluent.

TABLE 2

| Component | Mass Flow at Feed into the First Stabilization Zone in kg/h (lbs/h) | Mass Flow in $C_{4-}$ liquid stream in kg/h (lbs/h) |
|---|---|---|
| $C_3$ | 7,277 (16,043) | 5,446 (12,007) |
| i-$C_4$ | 21,191 (46,719) | 19,985 (44,060) |
| n-$C_4$ | 7,800 (17,197) | 7,204 (15,883) |

In the second theoretical modeling, the chilling zone had a temperature of approximately −17.7° C. (0° F.) and both the first modeling and the second modeling assumed 90% recovery of $C_4$ hydrocarbons from the second stabilization zone. Thus, as will be appreciated by those of ordinary skill in the art, the chilling zone further increases the recovery of the $C_4$ hydrocarbons. However, in either embodiment, the $C_4$ hydrocarbon recovery is accomplished without the need of an additional LPG stripper section to remove the HCl contained in the $C_4$ hydrocarbons liquid stream that was generated in the first isomerization zone.

Additionally, since the $C_4$ hydrocarbons that were produced in the first isomerization zone are not being processed in the $C_3-$ hydrocarbons stream passed to downstream processing, the processing units associated with same, for example, the a saturated gas plant recovery unit, can be smaller. This will allow for an increase in capital savings with smaller equipment and an increase in operating expense savings with requiring less energy to operate.

Finally, although various embodiments above were discussed with respect to the isomerization of iso-paraffins into normal paraffins, it is contemplated that the process could also be used in association with isomerization zones for isomerizing normal paraffins into iso-paraffins, with the same or similar benefits being realized.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for the recovery of $C_4$ hydrocarbons comprising:
   stabilizing and separating a first effluent stream in a first stabilization zone into an overhead stream, a $C_{4-}$ liquid stream, and a bottoms stream, wherein the first effluent stream is from a first isomerization zone;
   stabilizing a second effluent stream from a second isomerization zone in a second stabilization zone;
   passing at least a portion of the $C_{4-}$ liquid stream to the second stabilization zone; and,
   separating the second effluent stream and the at least a portion of the $C_{4-}$ liquid stream into a $C_4$ stream and a $C_{3-}$ stream.

2. The process of claim 1 further comprising:
   separating the $C_4$ stream into an $iC_4$ stream and a $nC_4$ stream.

3. The process of claim 2 further comprising:
   passing the iC4 stream to the second isomerization zone.

4. The process of claim 1 wherein the first stabilization zone comprises a stabilizer, a receiving zone and a chilling zone.

5. The process of claim 4 further comprising:
   passing a $C_{4-}$ stream from the stabilizer to the receiver;
   separating the $C_{4-}$ stream in the receiver into a vapor stream and a liquid stream, the liquid stream comprising the $C_{4-}$ liquid stream.

6. The process of claim 5 further comprising:
   cooling the vapor stream from the receiver in the chilling zone.

7. The process of claim 5 further comprising:
   combining a portion of the vapor stream from the receiver and the $C_{3-}$ stream of the second stabilization zone.

8. The process of claim 1 further comprising:
   operating the first isomerization zone under isomerization conditions, in the presence of a catalyst, to convert iso-paraffins into normal paraffins.

9. The process of claim 8 wherein the iso-paraffins comprise iso-pentane and iso-hexane.

10. The process of claim 9 further comprising:
    operating the second isomerization zone under isomerization conditions, in the presence of a catalyst, to convert iso-butane into normal butane.

11. A process for the recovery of $C_4$ hydrocarbons comprising:
    passing a $C_{4-}$ liquid stream to a stabilization zone, the liquid $C_{4-}$ stream comprising at least a portion of an effluent from a first isomerization zone for isomerization of $C_{5+}$ hydrocarbons operated under isomerization conditions to convert iso-paraffins into normal paraffins, wherein the $C_{4-}$ liquid stream is generated by separation of the effluent from the first isomerization zone;
    passing at least a portion of a second effluent stream from a second isomerization zone for isomerization of $C_4$ hydrocarbons to the stabilization zone, the second effluent stream comprising $C_{4-}$ hydrocarbons, wherein the second isomerization zone is operated under isomerization conditions to convert iso-butane into normal butane; and
    separating the at least a portion of the second effluent stream and the $C_{4-}$ liquid stream into a $C_4$ stream and a $C_{3-}$ stream in the stabilization zone.

12. The process of claim 11 wherein the iso-paraffins comprise iso-pentane and iso-hexane.

13. The process of claim 12 further comprising:
    cooling a portion of the effluent from the first isomerization zone to increase an amount of $C_4$ hydrocarbons in the liquid $C_{4-}$ stream.

14. The process of claim 11 further comprising:
    combining a first vapor stream from the stabilization zone comprising a $C_{3-}$ stream with a second vapor stream comprising a second $C_{3-}$ stream wherein the second $C_{3-}$ stream is generated by separation of the effluent of the first isomerization zone.

15. The process of claim 14 wherein the second $C_{3-}$ stream comprises a portion of the effluent from the first isomerization zone.

16. The process of claim 11 further comprising:
    separating the $C_4$ stream from the stabilization zone into an $iC_4$ stream and an $nC_4$ stream.

17. The process of claim 16 further comprising:
    passing the $iC_4$ stream to the second isomerization zone.

18. The process of claim 11 further comprising:
    separating the effluent from the first isomerization zone into a $C_{4-}$ stream and a $C_{5+}$ stream; and,
    separating the $C_{4-}$ liquid stream from at least a portion of the $C_{4-}$ stream.

19. The process of claim 18, further comprising:
    separating the $C_{4-}$ stream into the $C_{4-}$ liquid stream and a $C_{3-}$ vapor stream.

20. The process of claim 19 further comprising:
    increasing an amount of $C_4$ in the $C_{4-}$ liquid stream by cooling the $C_{4-}$ stream.

* * * * *